United States Patent
Xie et al.

(10) Patent No.: US 9,975,849 B1
(45) Date of Patent: May 22, 2018

(54) GOSSYPOL L-ARGININE SCHIFF BASE COMPOUND WITH ANTITUMOR ACTIVITIES AND A METHOD OF PREPARING THE SAME

(71) Applicants: Xiaolin Xie, Xi'an (CN); Dezhu Zhang, Xi'an (CN); Chengyuan Liang, Xi'an (CN); Lei Tian, Xi'an (CN); Shunjun Ding, Xi'an (CN); Xingke Ju, Xi'an (CN)

(72) Inventors: Xiaolin Xie, Xi'an (CN); Dezhu Zhang, Xi'an (CN); Chengyuan Liang, Xi'an (CN); Lei Tian, Xi'an (CN); Shunjun Ding, Xi'an (CN); Xingke Ju, Xi'an (CN)

(73) Assignee: SHAANXI PANLONG PHARMACEUTICAL GROUP LIMITED BY SHARE LTD., Xi'an (CN)

( * ) Notice: Subject to any disclaimer, the term of this patent is extended or adjusted under 35 U.S.C. 154(b) by 0 days. days.

(21) Appl. No.: 15/798,877

(22) Filed: Oct. 31, 2017

(30) Foreign Application Priority Data

Mar. 27, 2017 (CN) .......................... 2017 1 0185860
Sep. 12, 2017 (CN) .......................... 2017 1 0815411

(51) Int. Cl.
*C07C 279/14* (2006.01)
*C07C 277/08* (2006.01)

(52) U.S. Cl.
CPC .......... *C07C 279/14* (2013.01); *C07C 277/08* (2013.01); *C07B 2200/13* (2013.01)

(58) Field of Classification Search
CPC .. C07C 279/14; C07C 277/08; C07B 2200/13
See application file for complete search history.

(56) References Cited

PUBLICATIONS

Tian et al., "General, Green, and Scalable Synthesis of Imines from Alcohols and Amines by a Mild and Efficient Copper-Catalyzed Aerobic Oxidative Reaction in Open Air at Room Temperature," Adv. Synth. Catal. 2012, 354, 2671-2677.*

Liang et al., "Developing gossypol derivatives with enhanced antitumor activity," Investigational New Drugs 13: 181-186, 1995. (Year: 1995).*

* cited by examiner

*Primary Examiner* — Pancham Bakshi
*Assistant Examiner* — Mark R Luderer

(57) ABSTRACT

A compound with antitumor activities is represented by formula I:

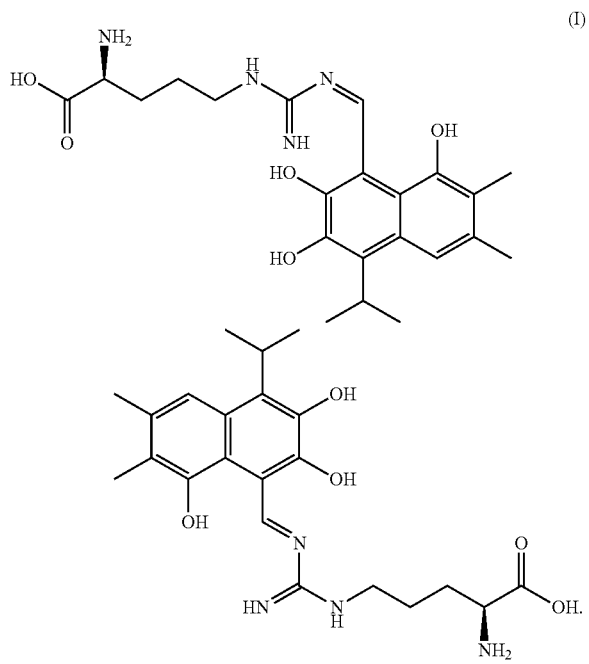

A method of preparing the compound of formula I is also disclosed.

11 Claims, No Drawings

GOSSYPOL L-ARGININE SCHIFF BASE COMPOUND WITH ANTITUMOR ACTIVITIES AND A METHOD OF PREPARING THE SAME

The present invention claims priority to Chinese Patent Application Nos. 201710185860.4, filed on Mar. 27, 2017, and 201710815411.X, filed on Sep. 12, 2017, which are incorporated by reference for all purposes as if fully set forth herein.

BACKGROUND OF THE INVENTION

Field of the Invention

The present invention relates to the field of pharmaceutical chemistry, and more particularly, to a gossypol L-arginine Schiff base compound with antitumor activities and a method of preparing the same.

Discussion of the Related Art

Gossypol is a polyphenolic bis-naphthalene aldehyde compound, and a natural yellow pigment found in small cell glands between cotton cells. Gossypol is an inhibitor of the Bcl-2 family of antiapoptotic proteins. It not only is an effective small molecule blocker of the Bcl-2, Bcl-xL and BH3 pockets, but also bins to Mcl-1 (Bcl-2 homologous protein).

L-arginine can effectively improve the immune system and promote the immune system to secrete natural killer cells, phagocytic cells, leukocyte interleukin (1) and other endogenous substances, beneficial to anti-cancer cells and preventing virus infection. In addition, L-arginine is a precursor of L-ornithine and L-proline. Recent studies have shown that the increase of L-arginine inhibits tumor cells and induces apoptosis. Some have tried to use imbalance amino acid therapy, adjust amino acid content in the tumor host body, interfere with tumor cell metabolism and function, and thereby inhibit tumor growth or induce apoptosis.

Schiff bases have unique structural characteristics, i.e., N atom in the core structure has a lone pair of electrons. The lone pair of electrons makes Schiff bases common ligands in coordination chemistry. Schiff bases can have two different groups that can react with various groups to obtain different derivatives, and can be used widely in chemical and biological applications.

The Schiff bases containing O, S, N atoms and its metal complexes have some antibacterial and antiviral activities and receive attention from researchers. The inventors propose that Gossypol and L-arginine form a twin drug, resulting in synergistic effect, enhancing the anti-tumor pharmacological activity. Accordingly, the inventors use L-arginine and gossypol as raw materials to design and synthesize a novel gossypol L-arginine Schiff base compound.

SUMMARY OF THE INVENTION

In one embodiment, the present invention provides a compound with antitumor activities represented by formula I:

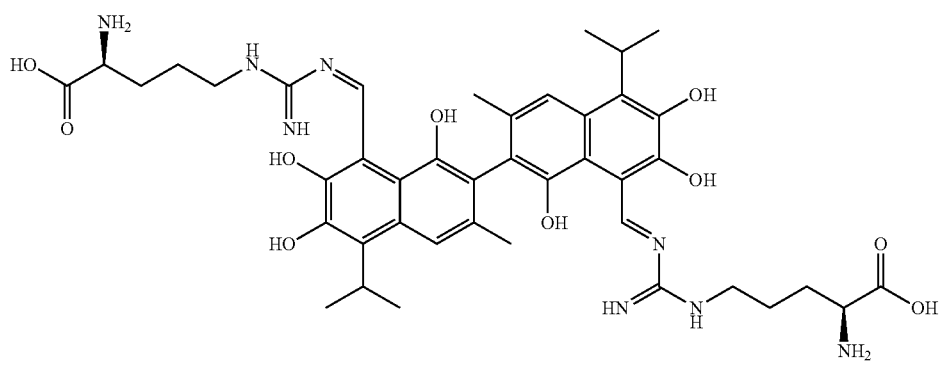

In another embodiment, the present invention provides a method of preparing a compound of formula I.

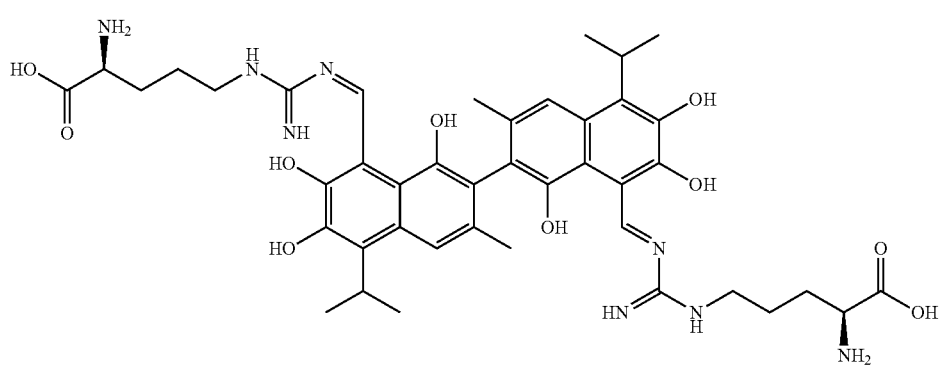

The method includes the following steps: 1) reacting compound 1 and compound 2 in an organic solvent in the presence of a catalyst; 2) filtering a reaction mixture of the compound 1 and the compound 2 and allowing the reaction mixture to stand for crystallization to obtain a crude product of the compound of formula I; and 3) recrystallizing the crude product in the organic solvent to obtain the compound of formula I.

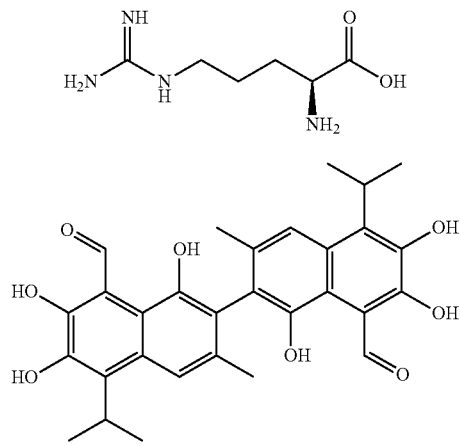

In another embodiment, the step 1) is conducted at 50-100° C.

In another embodiment, the step 1) is conducted at 60-80° C.

In another embodiment, the organic solvent is methanol, ethanol, or isopropanol.

In another embodiment, the organic solvent is ethanol.

In another embodiment, the catalyst is acetic acid, $ZnCl_2$, or p-toluenesulfonic acid.

In another embodiment, the catalyst is acetic acid.

In another embodiment, in the step 1), a molar ratio of the compound 1 and the compound 2 is 2:1 to 3:1.

In another embodiment, in the step 1), a molar ratio of the compound 1 and the compound 2 is 2.5:1.

In another embodiment, in the step 1), the compound 1 and compound 2 react for 2 hours.

It is to be understood that both the foregoing general description and the following detailed description are exemplary and explanatory and are intended to provide further explanation of the invention as claimed.

DETAILED DESCRIPTION OF THE ILLUSTRATED EMBODIMENTS

Reference will now be made in detail to embodiments of the present invention.

Disclosed are a novel gossypol L-arginine Schiff base compound with antitumor activities and a method of preparing the same.

In one embodiment, a compound with antitumor activities is represented by formula I:

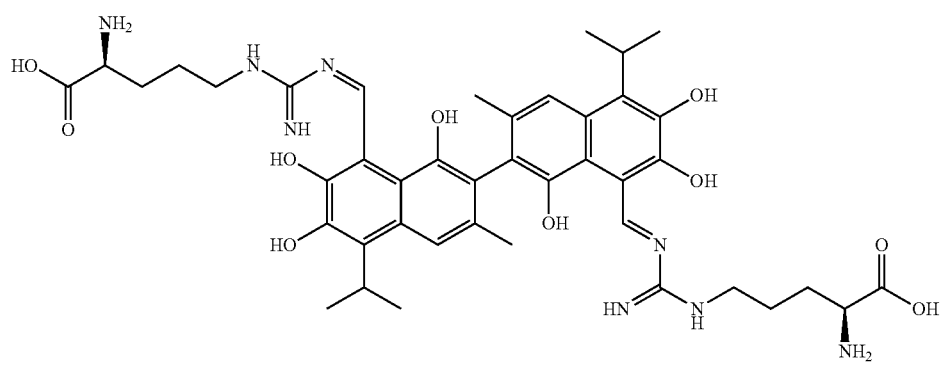

A method of preparing the compound of formula I is also disclosed.

The method uses L-arginine (compound 1) and gossypol (compound 2) as starting materials and ethanol as solvent under heating and refluxing.

The synthetic route is as follows:

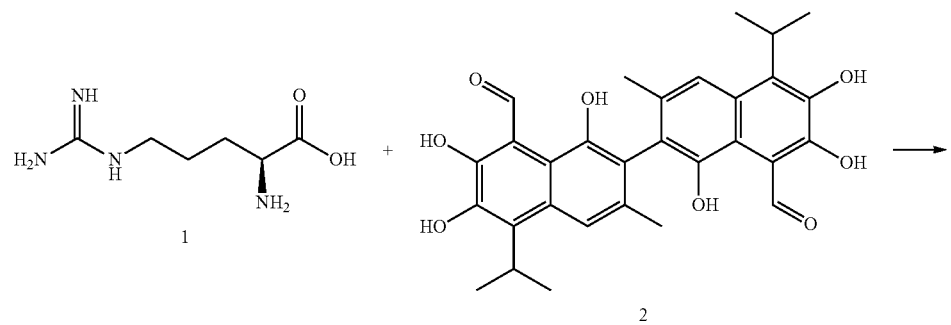

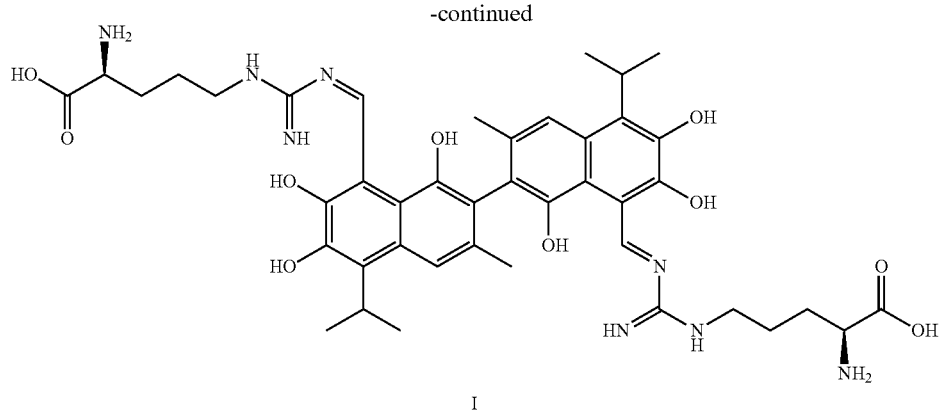

I

The synthesis route includes the following steps.

(1) L-arginine and gossypol, in a molar ratio of 2:1 to 3:1, were placed in three-necked flask. An appropriate amount of alcohol solvent was added. The mixture was mixed well under magnetic stirred. An appropriate amount of catalyst was added to the mixture, and the mixture was heated and refluxed at 50-100° C.

(2) Thin layer chromatography (TLC) method was used to track the reaction to completion. The hot reaction mixture was filtered and washed with an organic solvent. The filtrate was cooled to obtain a crude product of a gossypol L-arginine Schiff base compound.

(3) The crude product was placed in flask. Organic solvent was added for recrystallization. Filtration and drying gave desired product.

Preferably, in steps (1), (2), and (3) above, the organic solvent is methanol, ethanol, or isopropanol. More preferably, the organic solvent is ethanol.

Preferably, in step (1) above, the molar ratio of L-arginine and gossypol is 2:1 to 3:1. More preferably, the molar ratio is 2.5:1.

Preferably, in step (1) above, the reaction time is 2 hours.

Preferably, in step (1) above, the reaction temperature is 60-80° C.

Preferably, in step (1) above, the catalyst is acetic acid, $ZnCl_2$, or p-toluenesulfonic acid.

The advantages of the synthetic route are: inexpensive starting materials and environmental friendly, low production costs, mild reaction conditions and safe operation, suitable for industrial production.

INVENTIVE EXAMPLES

The invention will now be further elucidated with reference to specific embodiments. These examples are for illustrative purposes only and are not intended to limit the scope and spirit of the invention.

Example 1

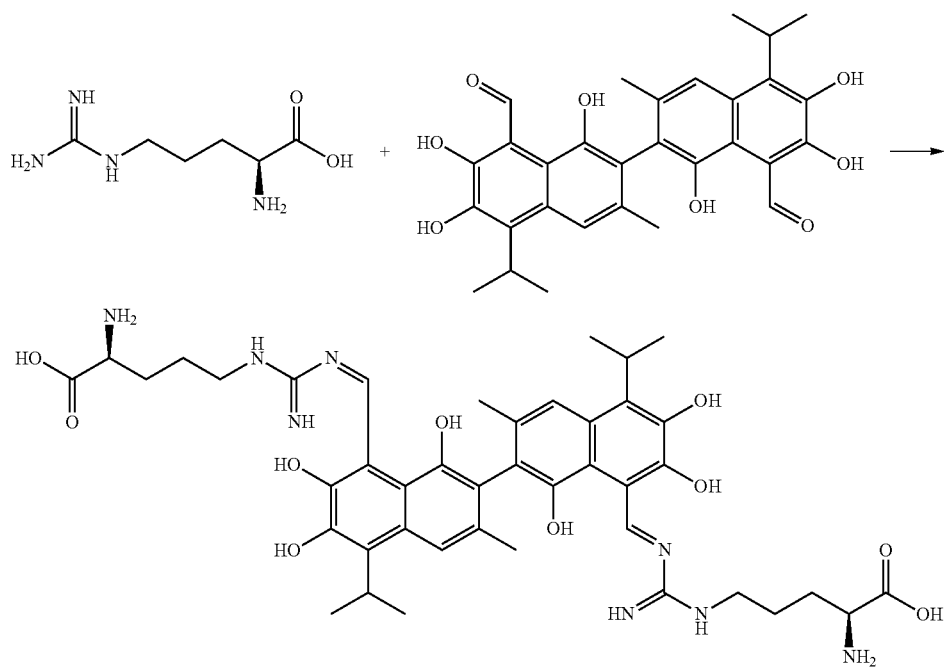

1.74 g (10 mmol) of L-arginine and 2.07 g (4 mmol) of gossypol were placed in a 100 mL three-necked flask. 50 mL anhydrous ethanol was added to the flask to dissolve the L-arginine and gossypol, and 3 drops of acetic acid was added as a catalyst. The mixture was heated at 60° C. with a water bath under magnetic stir. TLC was used to track the reaction to completion. The hot reaction mixture was filtered and washed with ethanol. The filtrate was cooled, filtered, and washed with ethanol three times to obtain a crude product. The crude product was recrystallized in anhydrous ethanol to give a yellow solid, 1.88 g, a yield of 56.61%.

Yellow crystalline powder. M.P. 182.3° C.; $^1$H-NMR (300 MHz, DMSO-d$_6$) δ(ppm): 13.76 (2H, s), 12.32 (2H, s), 10.31 (2H, s), 9.94 (2H, s), 9.58 (2H, s), 9.46 (2H, s), 8.75 (4H, d, J=7.8 Hz), 8.74 (2H, d, J=7.8 Hz), 8.25 (2H, s), 7.81 (2H, s), 3.42 (2H, q, J=8.0 Hz), 3.30 (2H, q, J=8.0 Hz), 2.87 (2H, m, J=7.8 Hz), 2.78 (6H, s), 1.75 (4H, q, J=7.8 Hz), 1.50 (4H, m, J=7.8 Hz), 1.33 (12H, d, J=7.8 Hz); $^{13}$C-NMR (101 MHz, DMSOd$_6$) δ(ppm): 175.7, 163.7, 153.4, 146.1, 153.4, 146.1, 144.1, 132.5, 130.7, 128.7, 119.0, 117.4, 112.2, 109.7, 101.4, 55.5, 37.9, 28.5, 27.1, 24.6, 24.0; MS (ESI) for (M+H)+: 831.4.

Example 2

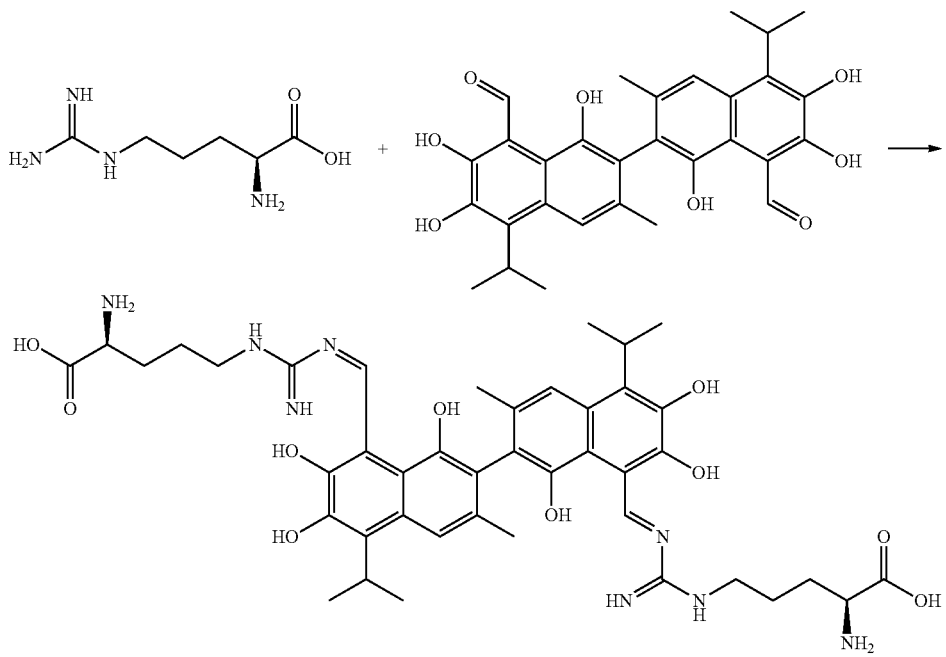

1.74 g (10 mmol) of L-arginine and 2.07 g (4 mmol) of gossypol were placed in a 100 mL three-necked flask. 50 mL anhydrous methanol was added to the flask to dissolve the L-arginine and gossypol, and 0.05 g of p-toluenesulfonic acid was added as a catalyst. The mixture was heated at 60° C. with a water bath under magnetic stir. TLC was used to track the reaction to completion. The hot reaction mixture was filtered and washed with methanol. The filtrate was cooled, filtered, and washed with methanol three times to obtain a crude product. The crude product was recrystallized in anhydrous methanol to give a yellow solid, 1.43 g, a yield of 43.06%.

Example 3

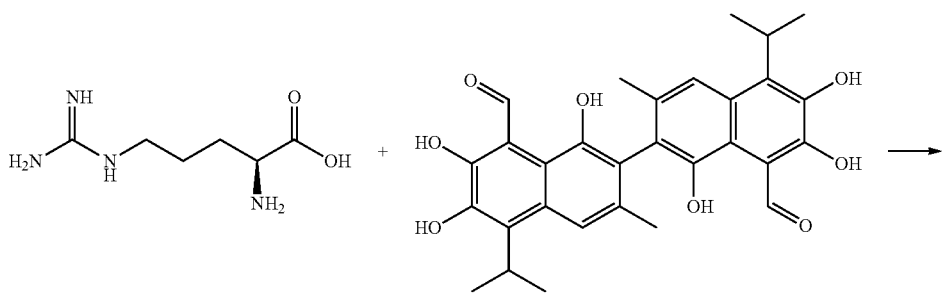

-continued

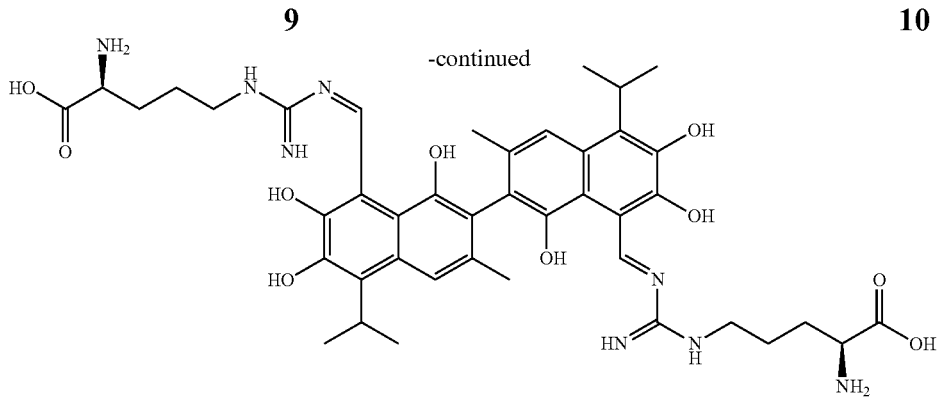

1.74 g (10 mmol) of L-arginine and 2.07 g (4 mmol) of gossypol were placed in a 100 mL three-necked flask. 50 mL anhydrous isopropanol was added to the flask to dissolve the L-arginine and gossypol, and 0.04 g (0.2 mmol) of $ZnCl_2$ was added as a catalyst. The mixture was heated at 80° C. with a water bath under magnetic stir. TLC was used to track the reaction to completion. The hot reaction mixture was filtered and washed with methanol. The filtrate was cooled, filtered, and washed with ethanol three times to obtain a crude product. The crude product was recrystallized in anhydrous ethanol to give a yellow solid, 0.97 g, a yield of 28.90%.

Example 4

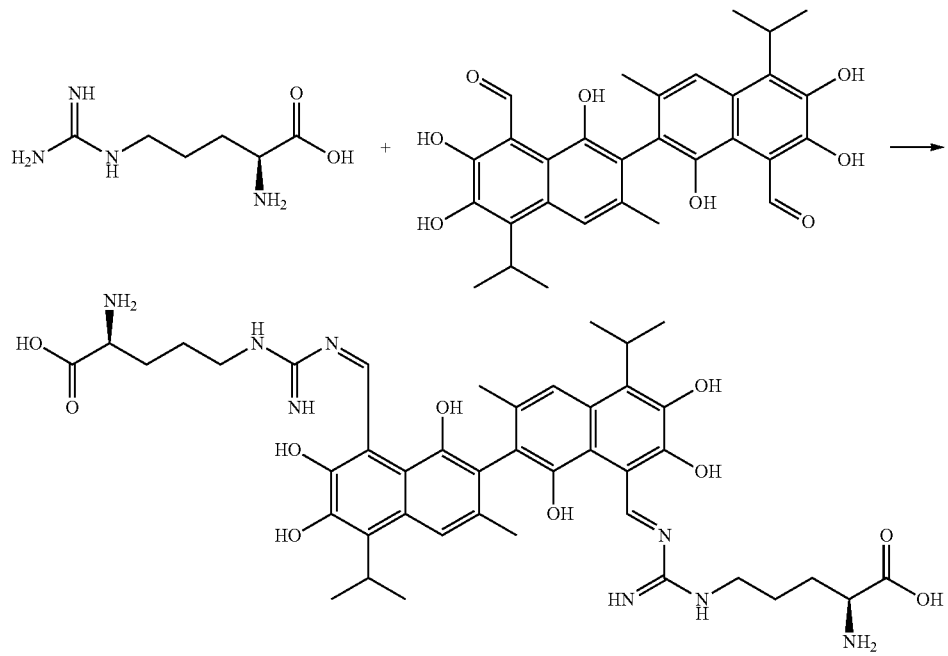

1.74 g (10 mmol) of L-arginine and 2.07 g (4 mmol) of gossypol were placed in a 100 mL three-necked flask. 50 mL anhydrous ethanol was added to the flask to dissolve the L-arginine and gossypol, and 0.04 g (0.2 mmol) of $ZnCl_2$ was added as a catalyst. The mixture was heated at 70° C. with a water bath under magnetic stir. TLC was used to track the reaction to completion. The hot reaction mixture was filtered and washed with methanol. The filtrate was cooled, filtered, and washed with ethanol three times to obtain a crude product. The crude product was recrystallized in anhydrous ethanol to give a yellow solid, 0.65 g, a yield of 19.40%.

Example 5

The Anti-Tumor Activity Test of the Compounds of the Present Invention

The compounds of the present invention were subjected to tumor cell proliferation inhibition test, and conventional MTT method was used.

Cell lines: human hepatoma cells (HepG2), human lung cancer cells (A-549), human gastric cancer cells (SGC-7901). The culture medium was DMEM+15% NBS+double antibody.

Sample solution preparation: after dissolving with DMSO (Merck), PBS (-) was added to obtain 100 µmol/L solution or homogeneous suspension. The solution was diluted with PBS (-) in DMSO to a final concentration of 0.1, 1, 10, 20, 40, 60, 80, 100 µmol/L.

Anti-uterine fibroids drug gossypol was used as control solution, prepared under the same condition.

Cell culture: adherent growth Tumor cells were cultured in 1640 medium containing 10% inactivated neonatal bovine serum and penicillin, streptomycin (1 million U/L), placed in carbon dioxide incubator at 37° C., 5% $CO_2$, and saturated humidity. Cells were treated serially passaged 2-3 times. The first culture was washed with PBS 2 times, and digested with trypsin. Fresh culture medium was added evenly, cells were adjusted to a appropriate concentration and transferred into a new culture flask. Cell in an exponential phase were chosen for the tests.

MTT Assay for Cell Viability and $IC_{50}$ Determination:

Experimental Principle: Living cells mitochondria in the dehydrogenase can reduce yellow MTT to water-insoluble blue-violet product MT (MTT formazan), deposited in the cells. The amount of production is proportional to the number of living cells. Dead cells do not reduce yellow MTT. DMSO can dissolve blue violet crystals, and the color depth is proportional to the amount contained, so the absorbance measured by the microplate reader can reflect the cell viability.

Methods: The exponential phase cells were digested and counted and seeded in 96-well plates at a density of $2 \times 10^4$/mL at 100 µl per well. After 24 hours of incubation, the cells to be tested were treated with 0.1, 1, 10, 20, 40, 60, 80, 100 µmol/L of the compounds. Each experimental group had 5 wells in each concentration, and the culture medium containing 0.4% DMSO was used as control. After 48 hours, the supernatant was discarded, and 100 µl of MTT ((2-(4,5-dimethyl-2-thiazolyl)-3,5-diphenyl-2H-tetrazole hydrobromide) (1 mg/mL) was added to each well. After another 4 hours, the supernatant was discarded, and 100 µl of DMSO was added to each well. After mixing, the absorbance was measured at 570 nm using a microplate reader. An $IC_{50}$ calculation software was used to determine the half inhibitory concentration ($IC_{50}$).

The test results are shown in Table 1. The compounds listed in the table correspond to the compounds described above.

TABLE 1

Half Inhibitory Concentration of Compounds on Different Tumor Cells $IC_{50}$
(unit: µmol/L)

| Compounds | $IC_{50}$ (µmol/L) | | |
|---|---|---|---|
| | HepG2 | A549 | SGC-7901 |
| Gossypol L-arginine Schiff base compound | 11.72 ± 0.32 | 12.34 ± 0.69 | 9.37 ± 0.36 |
| Gossypol | 8.29 ± 0.28 | 14.92 ± 0.64 | 18.17 ± 0.37 |

The results show that the gossypol L-arginine Schiff base compound has excellent antitumor activities in the three cell lines tested. Specifically, the compound has better antitumor activities than gossypol against A549 and SCG-7901. The above experimental results indicate that the gossypol L-arginine Schiff base compound of the present invention has good antitumor activities. The compound can be used for the study of antitumor research and drug development.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A compound with antitumor activities represented by formula I:

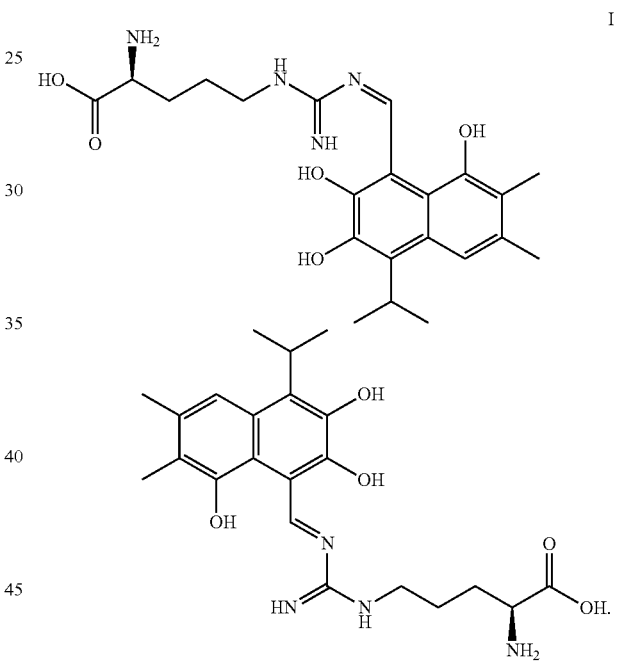

2. A method of preparing a compound of formula I comprising the following steps:

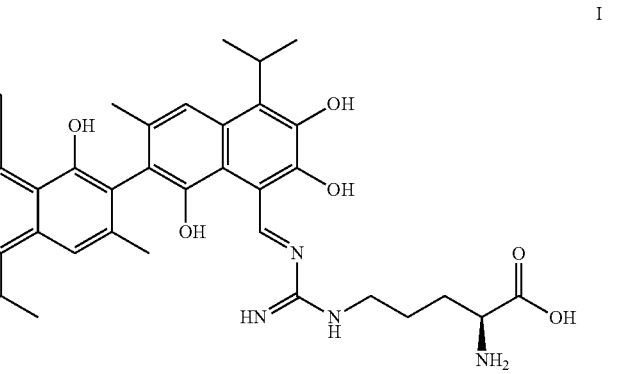

1) reacting compound 1 and compound 2 in an organic solvent in the presence of a catalyst;

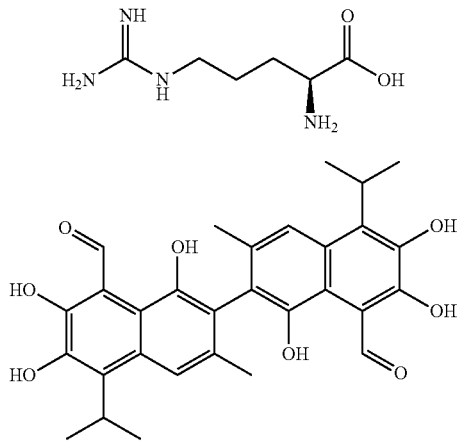

2) filtering a reaction mixture of the compound 1 and the compound 2 and allowing the reaction mixture to stand for crystallization to obtain a crude product of the compound of formula I; and 3) recrystallizing the crude product in the organic solvent to obtain the compound of formula I.

3. The reaction of claim 2, wherein the step 1) is conducted at 50-100° C.

4. The reaction of claim 3, wherein the step 1) is conducted at 60-80° C.

5. The reaction of claim 2, wherein the organic solvent is methanol, ethanol, or isopropanol.

6. The reaction of claim 5, wherein the organic solvent is ethanol.

7. The reaction of claim 2, wherein the catalyst is acetic acid, $ZnCl_2$, or p-toluenesulfonic acid.

8. The reaction of claim 7, wherein the catalyst is acetic acid.

9. The reaction of claim 2, wherein in the step 1), a molar ratio of the compound 1 and the compound 2 is 2:1 to 3:1.

10. The reaction of claim 9, wherein in the step 1), a molar ratio of the compound 1 and the compound 2 is 2.5:1.

11. The reaction of claim 1, wherein in the step 1), the compound 1 and compound 2 react for 2 hours.

\* \* \* \* \*